(12) United States Patent
Ten Kate (10) Patent No.: US 10,993,675 B2
(45) Date of Patent: May 4, 2021

(54) MONITORING A PHYSICAL OR MENTAL CAPABILITY OF A PERSON

(71) Applicant: KONINKLIJKE PHILIPS N.V., Eindhoven (NL)

(72) Inventor: Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 444 days.

(21) Appl. No.: 15/767,908

(22) PCT Filed: Oct. 18, 2016

(86) PCT No.: PCT/EP2016/074993
§ 371 (c)(1),
(2) Date: Apr. 12, 2018

(87) PCT Pub. No.: WO2017/067937
PCT Pub. Date: Apr. 27, 2017

(65) Prior Publication Data
US 2018/0310889 A1 Nov. 1, 2018

(30) Foreign Application Priority Data
Oct. 19, 2015 (EP) ..................................... 15190394

(51) Int. Cl.
*A61B 5/00* (2006.01)
*A61B 5/11* (2006.01)
*G16H 20/30* (2018.01)
*A61B 5/16* (2006.01)
*A61B 90/00* (2016.01)

(52) U.S. Cl.
CPC .......... *A61B 5/7275* (2013.01); *A61B 5/1113* (2013.01); *A61B 5/1118* (2013.01); *A61B 5/162* (2013.01); *A61B 5/6891* (2013.01); *A61B 5/743* (2013.01); *A61B 5/746* (2013.01); *G16H 20/30* (2018.01); *A61B 2090/064* (2016.02); *A61B 2503/08* (2013.01); *A61B 2505/07* (2013.01); *A61B 2562/0219* (2013.01); *A61B 2562/0247* (2013.01)

(58) Field of Classification Search
CPC ..... A61B 5/7275; A61B 5/1113; A61B 5/162; A61B 5/6891; A61B 5/743; A61B 5/746; A61B 2090/064; A61B 2503/08; A61B 2505/07; A61B 2562/0219; A61B 2562/0247; G15H 20/30
See application file for complete search history.

(56) References Cited

U.S. PATENT DOCUMENTS

| 6,108,585 A | 8/2000 | Kutzik et al. |
| 2005/0113650 A1 | 5/2005 | Pacione et al. |
| 2007/0123754 A1* | 5/2007 | Cuddihy ................ G16H 20/30 600/300 |
| 2015/0164377 A1 | 6/2015 | Nathan et al. |

FOREIGN PATENT DOCUMENTS

WO 20080135985 A1 11/2008

* cited by examiner

*Primary Examiner* — Lindsey G Wehrheim (57) ABSTRACT

Presented are concepts for monitoring a physical or mental capability of a person. One such concept employs the step of detecting a value of a property of the person or an object manipulated by the person. A trend in a physical or mental capability of the person may then be determined based on the detected value and historical data relating to one or more previously detected values of the property.

15 Claims, 6 Drawing Sheets

MONITORING A PHYSICAL OR MENTAL CAPABILITY OF A PERSON

This application is the U.S. National Phase application under 35 U.S.C. § 371 of International Application No. PCT/EP2016/074993, filed on Oct. 18, 2016, which claims the benefit of European Application Serial No. 15190394.5, filed Oct. 19, 2015. These applications are hereby incorporated by reference herein.

FIELD OF THE INVENTION

This invention relates to monitoring activities of daily living (ADLs) of a person and more particularly to monitoring a physical or mental capability of a person.

BACKGROUND OF THE INVENTION

Functional assessment or monitoring of a person's health status, physical abilities, mental abilities, or recuperation after injury, hospitalization and treatment is of primary concern in most branches of medicine, including geriatrics, rehabilitation and physical therapy, neurology and orthopaedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a person at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they live independently in their own home or within familiar surroundings. For example, one such known system for detecting activities of daily living of a person system comprises three main components: (i) a sensor system that collects information about the person's activities and behaviours; (ii) an intelligence (or information processing) system that interprets the sensor signals for determination of ADL behaviour; and (iii) a user interface system that enables care givers to inspect the interpreted (processed) information. The intelligence system typically makes use of computational techniques known in the art as artificial intelligence. The system may be supported by conventional technologies for data collection, transmission, and storage.

In practice, however, a major difficulty is encountered by the wide range of variations that can happen in actual care cases. Since there are so many possible circumstances, situations and contexts that can occur in daily life, it is common to employ numerous sensors in an attempt to capture enough information about a person's activities to enable identification of specific activities. This, however, typically increases costs and may therefore be undesirable.

The ever-increasing complexity in striving to cover all possible contexts and situations requires more elaborate and detailed information to be collected, processed, interpreted and/or communicated. Accuracy, or the amount of relevant information generated, may also be reduced by trying to cater for a large number of alternate situations. For example, although many situations may not be relevant to a monitored person, these irrelevant situations may still be accounted for and selected by the system, thus providing erroneous responses.

Also, a monitored person's physical and/or mental abilities may vary (e.g. decline or reduce) over time. As a result, it can be difficult to determine when some form of assistance, help of supervision may be needed.

SUMMARY OF THE INVENTION

The invention aims to at least partly fulfil the aforementioned needs. To this end, the invention provides devices, systems and methods as defined in the independent claims. The dependent claims provide advantageous embodiments.

There is provided an ADL monitoring system adapted to monitor a physical or mental capability of a person, wherein the ADL monitoring system comprises: a sensor adapted to detect a value of a property of at least one of: the person; and an object manipulated by the person; and to generate a sensor output signal representative of the detected value; and a monitor unit adapted to receive the sensor output signal, and to determine a trend in the physical or mental capability of the person based on the received sensor output signal and historical data relating to one or more previously detected values of the property.

Proposed is the concept of monitoring a physical or mental capability of a person by identifying a trend in the physical or mental capability using detected values of the person or an object manipulated by the person. By using a currently sensed value of a property, along with one or more previously detected values of the property, a trend, change or drift of the property may be identified. For example, by detecting a consistent change or pattern in detected values over time, a trend in a person's physical or mental capability may be inferred and, from this, current and/or future care/help/assistance requirements may be determined. Thus, there is proposed the concept of determining a trend in a person's capability based on current and historical values detected by a sensor. A detected value of property of the person and/or the monitoring may be used to infer a physical or mental capability of a person, and this may be undertaken numerous times over an extended time period (such as hours, days, weeks, months or years) so as to enable monitoring of the person's physical or mental capability over time. Furthermore, detected values (e.g. cumulative weight losses, reaction times, movement speeds, applied forces, etc.) for a predetermined timeframe (e.g. a week or month) may be used to estimate a trend in a physical or mental capability of the person for a current, following and/or preceding timeframe.

For example, weight measurements can be indicative of food or liquid consumption, and differences between consumption and/or weight measurement(s) may be used to identify pattern in a person's food/liquid consumption and/or weight variations that may, in turn, be used to infer a trend in a physical or mental capability of the person. For instance, sudden weight loss/gain outside of acceptable range of an established trend may indicate the occurrence of a problem/issue with a physical capability (such as walking or running), or, worse, the health, of the person.

A trend in the physical or mental capability of a person may therefore be inferred using a single sensor (e.g. a weight scale) at a single location (e.g. a toilet). This may help to reduce associated cost and/or complexity of an ADL monitoring system. For example, conventional ADL monitoring systems may be adapted to detect or monitor eating and drinking by employing sensors installed on a refrigerator (e.g. an open-close sensor), sensors installed in cupboards/drawers holding cutlery/food, power sensors on cooking equipment, presence sensors for detecting a user's presence in kitchen; a pressure sensor installed in a seat of a dining table, etc. Conversely, embodiments may avoid the need for multiple sensors (and complex signal processing of their respective signals) and may instead simply employ a single value (e.g. weight) sensing arrangement.

Embodiments may therefore enable for the monitoring of a person's physical or mental capability by detecting furniture activity (e.g. usage of items of furniture) and inferring a trend from detected changes in activity, such as changes in the frequency, speed, pattern, applied forces or ease of usage of the furniture.

Activities of daily living concern basic activities that a person executes on a regular basis. Examples of activities of daily living are drinking/eating; cooking; medicating; sleeping; toileting; bathing; washing, any kind of exercising such as walking, leisure activities such as reading or TV watching and many more etc. Thus, the invention may provide a way to monitor an ADL (such as cooking, eating, exercising, opening doors, etc.) in a simple and easy to implement manner.

The property of the person or the object may comprise at least one of: a velocity (e.g. translational and/or rotational) or speed of movement of the person or the object; a measure (such as magnitude, speed/rate of change, average, etc.) of force (or derivatives thereof) applied by the person to the object; a distance travelled by the object or a body part of the person;

a rate of acceleration of the object or body part of the person; a reaction time of the person; a measure of posture of the person; a height of the person; and a bodyweight of the person. By detecting values of a property of a person and/or an object that the person interacts with, a trend in the detected values over time may be identified and, from such a trend, a physical or mental capability of a person may be monitored.

For example, a trend of declining/decreasing velocity or speed of movement of the person (as detected directly or inferred using a accelerometer affixed to the person, or as detected indirectly using a accelerometer integrated into an object that is moved by the person) may be used to identify and monitor the person's physical strength or speed, and further identify a future point in time where the person's physical strength or speed declines to a point where assistance or help will be required. By way of another example, a trend of increasing reaction time of the person (as detected using a timing device that detects an amount of elapsed time between a prompt or signal and a response from the person) may be used to identify and monitor the person's physical or mental capability in responding to a command, and further identify a future point in time where the person's capability will reduce to a level where additional assistance or help will be required. For example, predictive analytics may be employed to try and identify (and thus prevent or avoid) undesirable or worst case outcomes. This may help to provide cost savings (e.g. in a health care system) by timely enabling intervention. Embodiments may therefore be useful for identifying future requirements of a monitored person, and this may be achieved via extrapolation of a trend determined by a proposed embodiment.

Embodiments may be further adapted to store the sensor output signal(s) in a database adapted to store historical data relating to one or more previously detected values of the property. Previously determined values of a property of the person or the object may therefore be stored, in a historical database for example, and then used in subsequent calculations. Furthermore, currently detected values may be used to re-calculate or refine a previously determined trend.

The monitor unit may be further adapted to detect an irregularity in the determined trend. The monitor unit may then generate an alert output signal in response to the detected irregularity.

To detect an irregularity, the monitor unit may undertake a comparison of the determined trend with a threshold value. For example, the monitor unit may employ a data processing unit that compares the determined trend with a threshold value and then generates a warning signal if the determined trend exceeds the threshold value. The threshold may be preprogrammed and fixed, but it may be preferable to enable the threshold value to be set by a user preference. Also the threshold value may relate to a future value, and the trend may be extrapolated for comparison of an extrapolated value with the future threshold value. This may identify when a threshold value may be exceeded in the future, for example.

In an embodiment, the monitor unit may be further adapted to calculate an estimated future value of the property based on the determined trend, and the monitor unit may be further arranged to detect an irregularity based on a comparison of the estimated future value of the property with a threshold value and to generate an alert output signal in response to the detected irregularity.

Embodiments may therefore further comprise a user input interface adapted to receive a user input for defining or modifying one or more alert conditions, and the monitor unit may be adapted to generate an alert output signal based on the determined trend and the one or more alert conditions.

Further, the threshold may be based on previously detected values and/or a previously determined trend in a physical or mental capability of the person. For instance, the threshold value may be determined based on at least one of: one or more previously detected values of the property; and one or more previously determined changes in values of the property. In other words, the threshold may be defined by taking account of a history of detected values and/or a history of changes in values of the property so that it can be used to identify outlying values or anomalies.

Embodiments may be adapted to provide the generated alert output signal to at least one of: the person; a medical practitioner; and a caregiver.

Also, the threshold value may be enabled to be set to act on a person to be monitored or act on a group of persons to be monitored.

The monitor unit may be further adapted to generate a control signal for modifying a graphical element based on the determined trend in the physical or mental capability of the person. Further, the ADL monitoring system may further comprise a display system adapted to display the graphical element in accordance with the control signal generated by the monitor unit. In this way, a user (such as a care giver) may have an appropriately arranged display system that can receive and display information about the trend in the physical or mental capability of the person, and that person may be remotely located from the user. Embodiments may therefore enable a user to remotely monitor a person using a portable display device, such as a laptop, tablet computer, mobile phone, PDA, etc.

It will be appreciated that all or part of the monitor unit may comprise one or more data processing units. For example, the monitor unit may be implemented using a single processor which is adapted to undertake data processing in order to determine a trend in the physical or mental capability of the person (based on the received sensor output signal and historical data relating to one or more previously detected values of the property). The monitor unit may be remotely located from the sensor, and a signal representative of the signal representative of the detected value may be communicated to the monitor unit via a communication link.

The system may further comprise: a server device comprising the monitor unit; and a client device comprising the sensor. Dedicated data processing means may therefore be employed for the purpose of determining a trend in the physical or mental capability of the person, thus reducing processing requirements or capabilities of other components or devices of the system.

The system may further comprise a client device, wherein the client device comprises the monitor unit and a display system. In other words, a user (such as a care giver) may have an appropriately arranged client device (such as a laptop, tablet computer, mobile phone, PDA, etc.) which processes received data in order to determine a trend in the physical or mental capability of the person.

Thus, processing may be hosted at a different location from where the sensing happens. For example, for reasons of power efficiency (e.g. to improve battery lifetime) it might be advantageous to execute only part of the processing at the sensor location, thereby reducing associated costs, processing power, transmission requirements, etc.

Thus, it will be understood that processing capabilities may therefore be distributed throughout the system in different ways according to predetermined constraints and/or availability of processing resources.

The sensor arrangement/system may be positioned in a strategic position so that it detects the appropriate value without the person needing to intentionally or consciously activate/operate the sensor. In this way, a person may only need to undertake their normal activities. Such strategic positioning may ensure that a value of a property of the person or environment can be automatically and accurately obtained, and this may not require the person to remember to undertake any special or additional activities in order for a value to be detected by the sensor. This may remove the risk of the person forgetting to activate a sensor (e.g. by pressing a button), for example.

There exist many sensors that can be employed by an ADL monitoring system according to an embodiment. Typical sensors include PIR (Passive Infra-Red; measure movement and presence), OC (open-close; measure state of doors, in particular front doors, windows, and cupboards, including refrigerators), power sensors (measure current consumption of appliances, such as microwave, water cookers, TV, etc); and pressure sensors or mats (measure occupancy of user sitting in chair, lying in bed, standing on door mat in front of front door, being at toilet, etc). Many others exist and are conceivable, such as sensors to signal light switch state, or sensors that measure environmental conditions such as humidity, CO2 level (or CO and smoke), Particulate Matter level, etc. A further range of sensors are those based on physical quantities, such as accelerometers, magnetometers, gyroscopes, and air pressure sensors. Accelerometers, for example, can also measure state of doors and their open-close movements or measure speed or velocity of movement of a person or an object moved by the person. Yet another range of sensors consists of microphones and cameras (including infra-red, or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home system.

Although the sensor(s) may be mounted in the monitoring environment (e.g. the person's home), they may also be attached to user utilities (such as a keyring) or put in clothes, in a pocket or bag, or as insole or undergarment, etc. They may also be fabricated to be worn explicitly like a wrist watch or pendant. Further, the sensors may communicate their output signals via a wired or wireless connection, or a combination thereof. Accordingly, in an embodiment, the sensor may be adapted to be coupled to the person or the object. The object may for example comprise an item of furniture (such as a fridge, cupboard, wardrobe, seat, door, white good, etc.) adapted to be used in the execution of an ADL.

The sensors may also be adapted to undertake primary processing of the detected values, such a signal filtering, sampling, conditioning, etc., so as to reduce required transmission bandwidth and/or transmission duration for example. Alternatively, the sensors can send raw data.

Non-intrusive monitoring may therefore be realized with relatively simple sensors that provide data on specific ambient conditions or properties/parameters of an object, an environment (such as temperature or humidity for example), or properties of the person (such as movement, weight, speed, weight, and/or distance travelled for example). Such sensors for measuring ambient condition or properties/parameters of the object or environment may be simple, small and/or cheap. Also, the movement of the person may be detected with, for example, a Passive Infrared (PIR) sensor which is a cheap component. Movement sensors may be used to switch on lighting and people are therefore typically familiar with their usage.

Thus, ADL monitoring systems of the invention may employ conventional sensors and/or existing sensor arrangements. Also, embodiments may employ sensors that are considered to be non-intrusive and more easily accepted by the monitored person. Yet, with the data provided by these sensors, ADLs may be determined and provide information on the person being monitored.

Such sensors may be employed by, or in conjunction with, embodiments so as to increase the number and/or accuracy of monitored ADLs. They may also be used to confirm or qualify readings taken by a sensor, so that spurious or unintentional measurements are avoided. For example, signals from a location sensor worn by the monitored person may be used to confirm if weight readings taken by a weight sensing system are indeed attributable to the monitored person or some other person or animal (such as their pet), for example.

There is provided a method of monitoring a physical or mental capability of a person, wherein the method comprises: detecting a value of a property of at least one of: the person; and an object manipulated by person; and determining a trend in the physical or mental capability of the person based on the detected value of the property and historical data relating to one or more previously detected values of the property.

Embodiments may further comprise: detecting an irregularity in the determined trend, and generating an alert output signal in response to the detected irregularity.

The step of detecting an irregularity may comprise: detecting an irregularity based on a comparison of the determined trend with a threshold value.

There is provided a computer program product for monitoring a physical or mental capability of a person, wherein the computer program product comprises a computer-readable storage medium having computer-readable program code embodied therewith, the computer-readable program code configured to perform all of the steps of an embodiment.

A computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of the method of controlling an ADL monitoring system display unit according to an embodiment.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying schematic drawings, in which.

DETAILED DESCRIPTION OF THE EMBODIMENTS

Proposed is a concept for monitoring a person by determining a trend in the physical or mental capability of the person, which may be useful for the purpose of unobtrusively monitoring the well-being of the person for example. Such persons may, for instance, include a disabled person, an elderly person, an injured person, a medical patient, etc. Elderly persons can mean persons above 65 years, above 70, or above 80 years old.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

In general, to be able to observe trends in "normal" daily behavior of a person one may monitor ADLs of a person. From established trends, one may also spot unexpected activities, anomalies or deviations from expected values or patterns. The type of anomaly or irregularity can be different per case.

A large class of physical or mental capabilities can relate to an ADL routine of the person. For example, a physical capability may be inferred from the speed by which a person opens/closes a door (or a cupboard, wardrobe, fridge, microwave, or other furnishings) or a drawer and/or the force applied to the door or drawer during the opening/closing process.

Embodiments of the present invention are directed toward enabling information about a physical or mental capability of a person to be obtained and potentially monitored. Such information may therefore be useful for monitoring the health or well-being of a person.

Embodiments employ the concept of determining a trend in a physical or mental capability of a person from a current value of a property of the person or an object manipulated by the person and historical data relating to one or more previously detected values of the property. In other words, determination of a trend in a physical or mental capability of a person may be based on current and previously detected properties of the person or an object manipulated by person. Such properties may relate to the strength, speed, coordination of the person, and may be detected by one or more sensors that detect a force exerted by the person, a speed of a body part of the person or the object, angular velocity of a body part of the person or the object, the weight of the person, and the like, and this may be undertaken in relation to particular ADLs.

A trend in a physical or mental capability of a person may therefore be determined using a single sensor (e.g. an accelerometer) installed at a single location (e.g. a door or drawer), thus reducing the burden, cost and/or complexity of a system according to an embodiment. It may also help to ensure anomalies are accurately detected, thus improving the accuracy of monitoring results. Such a proposed concept for monitoring a physical or mental capability of a person may therefore be employed in a system for monitoring ADLs of a person within an environment.

Physical or mental capabilities may be detected or inferred from sensor output signals and there already exist systems and methods for such detection or inference. Accordingly, the proposed concepts may be used in conjunction with existing ADL detection or monitoring systems/methods. For example, Dries Vermeiren et al describe a system based on 2 tri-axial accelerometers to detect the ADLs of a patient in a paper entitled "Detecting Human Motion: Introducing Step, Fall and ADL algorithms". Also, H Pirsiavas et al describe algorithms for detecting ADLs in first-person camera views in paper entitled "Detecting activities of daily living in first-person camera views" (CVPR, 2012). Because many such ADL detection or monitoring methods/systems are known and any one or more of these may be employed, detailed description of such methods/systems is omitted from this description.

Figure 1:
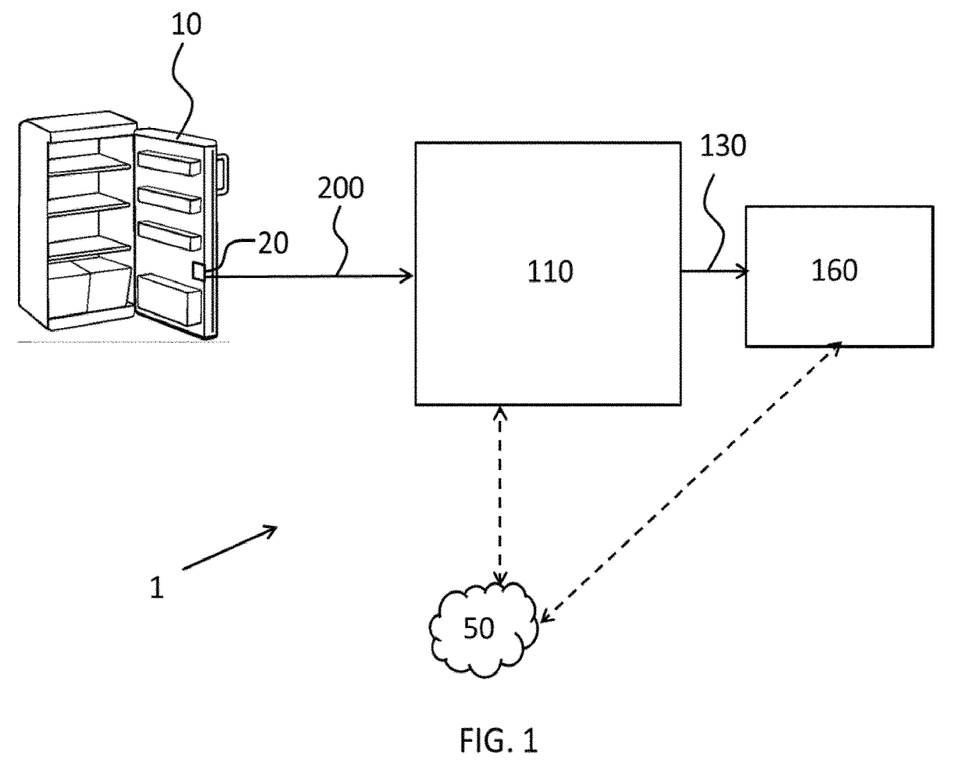
FIG. 1 is a simplified block diagram of a system adapted to monitor a physical or mental capability of a person according to an embodiment.

FIG. 1 shows an embodiment of a system 1 according to the invention comprising a fridge door 10 and a motion sensor 20 adapted to detect a velocity of the fridge door 10 which results from the person's usage (e.g. opening or closing) of the fridge door 10.

Here, the motion sensor 20 is situated integrated into the fridge door 10 so that it moves with the fridge door 10. For example, the motion sensor 20 may comprise an accelerometer, magnetometer, and gyroscope. A gyroscope is of particular interest when the fridge door 10 is a rotating one (i.e. hinged at one side to that it is rotated about a vertical axis when opened/closed) like that shown in FIG. 1. Since a gyroscope measures rotation velocity, it can be mounted at any spot of the fridge door 10. For example, it can be mounted close to the hinge or rotation axis so that is hidden from sight, or it can be mounted far from the hinge (e.g. close to the handle of the fridge door shown in FIG. 1) so that it can be accessed easily (for repair or replacement for example).

In this way, a person need only undertake their normal activities when using the fridge and may not even be aware that they are operating the motion sensor and being monitored. Such positioning (integrated into the fridge door 10, for example) may ensure that a property of the person or the fridge door 10 (such as: a velocity or speed of movement of the door 10; a magnitude of force applied by the person to the door 10; a distance travelled by the door 10; a rate of acceleration of the door 10; the duration of opening/closing of the door; the impulse (integrated force/acceleration); or the (peak) power (force/acceleration time velocity) exercised during open and/or close, for example) can be automatically and accurately obtained for each single usage (e.g. opening or closing) of the fridge (e.g. every time the person accesses the contents of the fridge) without requiring the person to remember to undertake any special or additional activities in order for a property of the person or the fridge door 10 to be detected. For example, it can remove the need for a person to perform a specific additional action (e.g. pressing a button) in order to activate the motion sensor 20.

The motion sensor 20 comprises a motion sensing arrangement that is adapted to determine a velocity of movement of the fridge door 10, a distance travelled by the fridge door 10, and a rate of acceleration of the fridge door 10, when the fridge door 10 is opened. The motion sensor 20 may obtain numerous measurements before, during and after the person opens or closes the fridge door.

The motion sensor 20 is adapted to output sensor output signals 200 which are representative of the detected value(s) of the fridge door 10 during opening or closing. Of course, many more sensors may be employed so as to provide signals indicative of detected values of properties of the person and/or the fridge door. For example, the magnitude of a pulling or pushing force applied by the person to the fridge door may be detected using one or more pressure sensors. Such additional signals may be useful for identifying which of the sensor output signals 200 are indicative of a property of the person or the fridge door 10. They may also be used to confirm or qualify values detected by the motion sensor 20, so that spurious or unintentional measurements are avoided. For example, signals from a location sensor worn by the monitored person may be used to confirm if values detected by the motion sensor 20 are indeed attributable to the monitored person operating the fridge door 10, for example.

The motion sensor 20 communicates its output signals 200 via a wired or wireless connection. By way of example, the wireless connection may comprise a short-to-medium-range communication link. For the avoidance of doubt, short-to-medium-range communication link may be taken to mean a short-range or medium-range communication link having a range of up to around 100 meters. In short-range communication links designed for very short communication distances, signals typically travel from a few centimeters to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), Near Field Communication (NFC), RFID, 6LoWPAN, UWB, Wireless HART, Wireless HD, Wireless USB, ZigBee. Examples of medium-range communication links include Wi-Fi, ISM Band, Z-Wave. Here, the output signals are not encrypted for communication via the wired or wireless connection in a secured manner. However, it will be appreciated that, in other embodiment, one or more encryption techniques and/or one or more secure communication links may be employed for the communication of signals in the system.

The system further comprises a data processing unit 110 adapted to receive the sensor output signals 200, and to determine a trend in the physical capability of the monitored person based on the received sensor output signals 200 and historical data relating to one or more previously detected values of the property (e.g. previously detected values of: a velocity of movement of the fridge door 10, a distance travelled by the fridge door 10, and a rate of acceleration of the fridge door 10, when the fridge door 10 is opened). For this purpose, the data processing unit 110 may communicate with one or more data processing resources available in the internet or "cloud" 50. Such data processing resources may undertake part or all of the processing required to infer or determine a trend in the physical capability of the monitored person based on the received sensor output signals 200 and historical data. Thus, the embodiment may employ distributed processing principles.

The data processing unit 110 is further adapted to generate an output signal 130 representative of an inferred or determined trend in the physical capability of the monitored person. In other words, after having a trend in the physical capability of the monitored person based on the received sensor output signals 200 and historical data (either with or without communicating with data processing resources via the internet or "cloud"), an output signal 130 representative of or determined trend in the physical capability of the person is generated.

The system further comprises a graphical user interface (GUI) 160 for providing information to one or more users. The output signal 130 is provided to the GUI 160 via wired or wireless connection. By way of example, the wireless connection may comprise a short-to-medium-range communication link. As indicated in FIG. 1, the output signal 130 is provided to the GUI 160 from the data processing unit 110. However, where the system, has made use of data processing resources via the internet or cloud 50), an output signal may be made available to the GUI 160 via the internet or cloud 50.

Based on the output signal 130, the GUI 160 is adapted to communicate information by displaying one or more graphical elements in a display area of the GUI 160. In this way, the system may communicate information about a trend in the physical capability of the monitored person that may be useful for indicating that the person is in need of attention or for estimating when the person may be expected to require assistance or attention. For example, the GUI 160 may be used to display graphical elements to a medical practitioner, a caregiver, a family member or close relative. Alternatively, or in addition, the GUI 160 may be adapted to display graphical elements to the monitored person.

Figure 2:
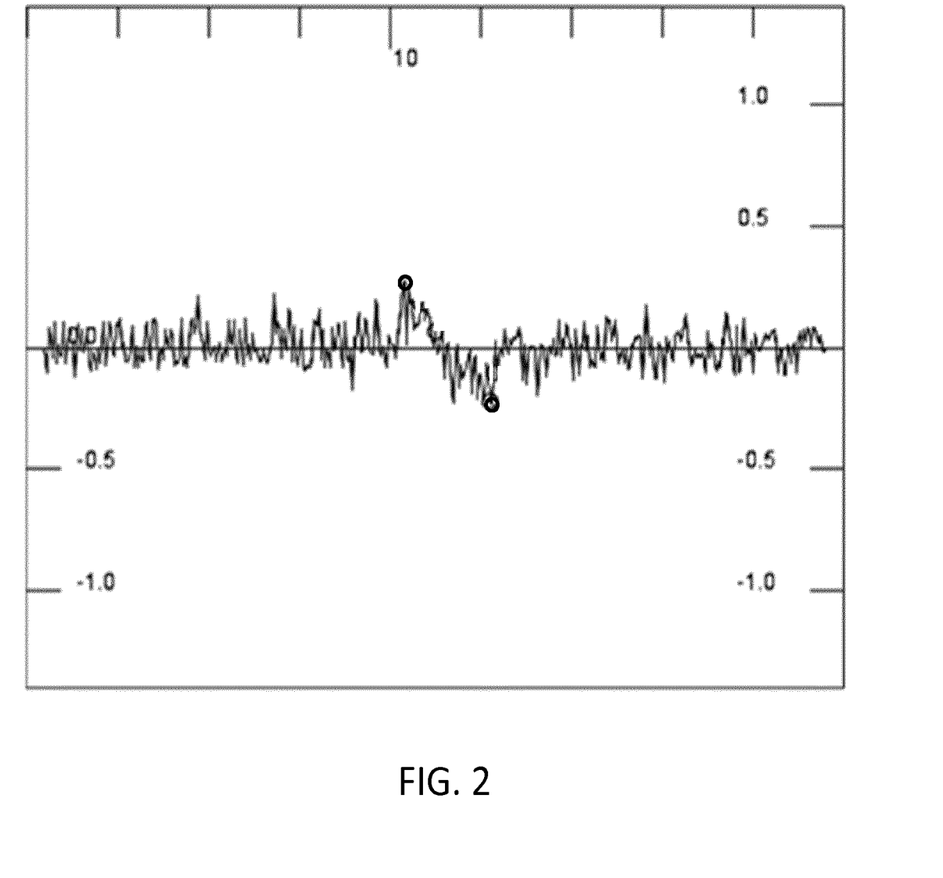
FIG. 2 is a graph depicting detected values of acceleration measured in metres per second per second over a time period (t) of twenty seconds according to an exemplary embodiment.
Figure 3:
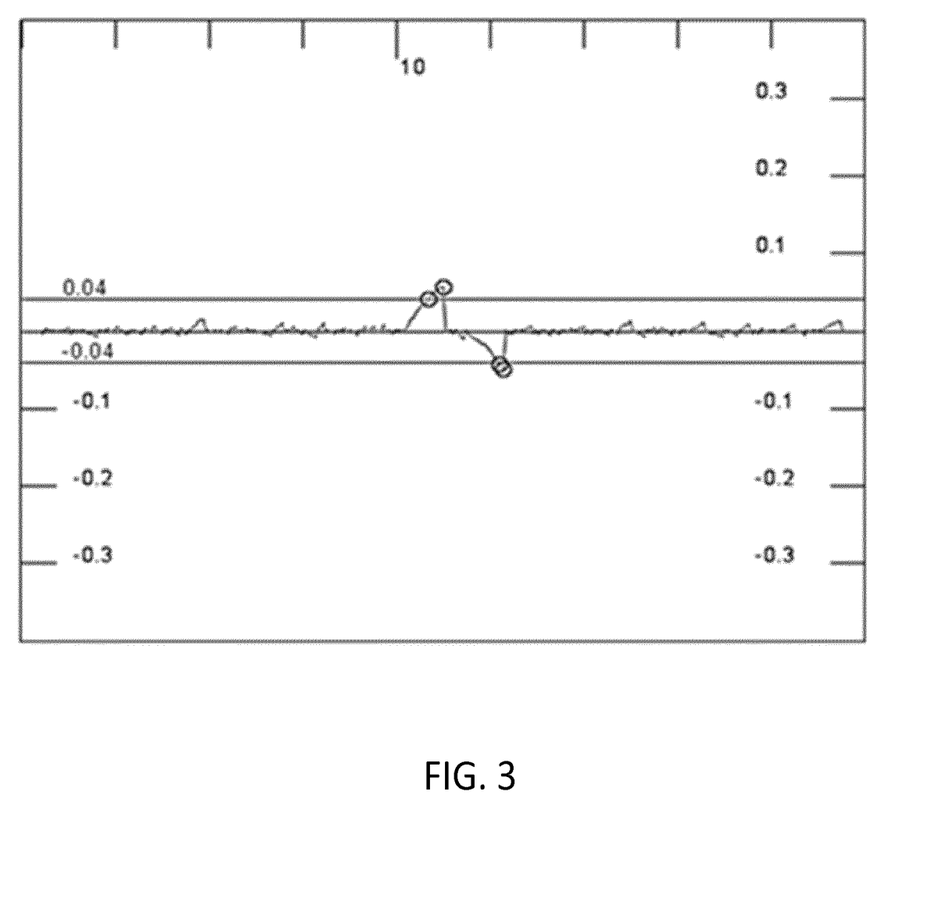
FIG. 3 is graph depicting the "area under curve" version derived from the detected values of FIG. 2.

Referring now to FIGS. 2 and 3, exemplary detected acceleration behaviour of a fridge door 10 (as detected by the system of FIG. 1) is illustrated using graphs.

The graph of FIG. 2 depicts the detected values of acceleration measured in metres per second per second over a time period (t) of twenty seconds. The detected peak values of interest are indicated using a circular-shaped identifier "0", and these may be identified based on another detected signal indicating that the fridge door 10 is being operated (e.g. a door open or close event) by the monitored person, from a location sensor for example.

The graph of FIG. 3 depicts the Area Under Curve (auc) version derived from the detected values of FIG. 2. This version is obtained by integrating the signal of FIG. 2 from zero crossing to zero crossing (e.g area under signal). By doing this, the open/close door movement becomes more visible, as illustrated in FIG. 3. The detected values of interest are indicated using a circular-shaped identifier "0".

Thus, FIG. 2 provides the acceleration signal, and thus enables the maximum (modular) acceleration values to be identified. FIG. 3 enables the maximum impulse/velocity (i.e. acceleration integrated) values to be identified. By way of further example, another signal may be derived by taking the product of the detected velocity and acceleration signals, namely power. A maximum exerted power may therefore be identified from such a signal.

The peak values of the signals (e.g. either graph of FIG. 2-3) can be used as current detected values for trend determination and/or analysis according to a proposed embodiment. By only using the peak values when an open or close event is detected, other (unrelated) signals are not used for trend determination and/or analysis.

The peak value(s) may also be stored in a database adapted to store historical data relating to one or more previously detected values (of acceleration of the fridge door 10). In doing so, each peak value (during an open/close event) may be labelled with the timestamp identifying when the value was measured. In the trend determination or analysis, the detected values may then be averaged per time unit, e.g. per day, before the trend is estimated.

Other embodiments may use the 3 (or 5, 6, 7 or any other positive integer) best values over the course of a predetermined time period (e.g. morning, afternoon, day, etc.), to use obtain an average value. Of techniques to centralised, representative, or average value may be used.

Given a (known) context, one may also exclude certain days. For example, on Fridays, the grandchildren or a cleaning lady are in the house and so detected data may not be representative of the monitored person.

Another approach may be to provide each detected value (or measurement) as a pair of time and value, so that trend analysis, using a regression method for example, may account for the varying rate (e.g. irregularity in arrival) at which values are detected.

Previously detected values of a property of the person or object manipulated by the person may be stored, in a database for example, and then used in current or subsequent trend calculations. Thus, by storing previous detected values, estimates of a trend in the values can be determined and a future date/time at which the person may require help or assistance may be identified (e.g. by extrapolating the trend to identify when it goes above/below a threshold value).

Furthermore, currently detected values may be used to re-calculate or refine previously determined trends (e.g. those stored in a database for example).

Although the embodiment described above employs sensors to detected properties of a fridge door that is manipulated by a monitored person, it will be understood that many other different properties of a person and/or object manipulated by the person may be detected using sensors (of the same or different type) in alternative embodiments. For example, other embodiments may be arranged to: detect a velocity or speed of movement of the person or the object; detect a magnitude of force applied by the person to the object; detect a distance travelled by the object or a body part of the person; detect a rate of acceleration of the object or body part of the person; detect a reaction time of the person; and/or detect a bodyweight of the person.

By detecting values of a property of a person and/or an object that the person interacts with, a trend in the detected values over time may be identified and, from such a trend, a physical or mental capability of a person may be monitored. For example, a trend of declining/decreasing force applied by the person to an object (as detected directly using a pressure sensing pad integrated into an object, such as a door pusher for example, or as detected indirectly using an accelerometer integrated into the object that is moved by the person) may be used to identify and monitor a trend in the person's physical strength.

Figure 4:
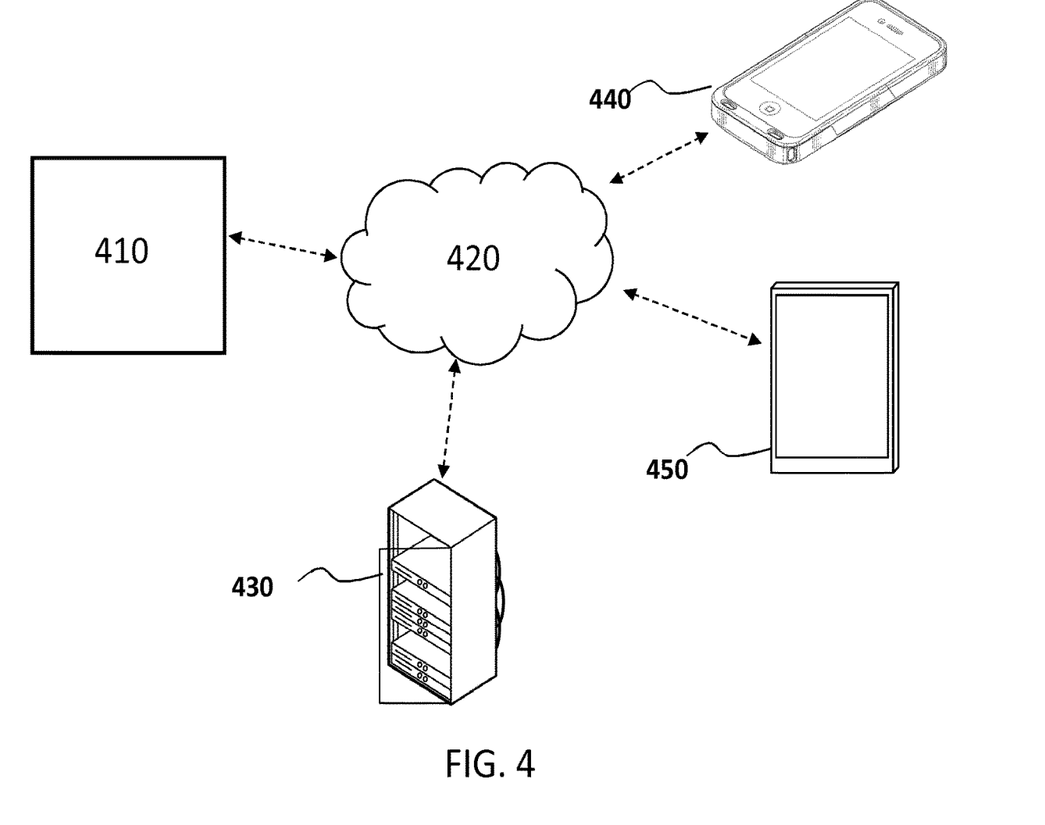
FIG. 4 is a simplified block diagram of a system according to an embodiment.

Referring now to FIG. 4, there is depicted another embodiment of a system according to the invention comprising a weight sensing system 410 adapted to detect a weight of the person. Here, the weight sensing system 410 comprises a high-resolution weight scale adapted to be integrated into a toilet (for example, within the toilet seat). The weight sensing system 410 is adapted to output one or more signals which are representative of the detected value(s) of a person's weight at least before or after using the toilet.

Although this embodiment has been described as integrating the weight sensing system 410 into the toilet, it will be understood that, in alternative embodiments, the weight sensing system 410 may be provided separately from the toilet such that it requires a person to be aware of the weight sensing system 410 and actively use the weight sensing system 410. Such an alternative arrangement may avoid the need for additional sensors (to confirm or qualify values detected by the weight sensing system, for example) and thus be more simple and/or cheaper. For example, instead of being integrated into the toilet, the weight sensing system may be positioned at the entrance or doorway to a room so as to measure a person's weight upon entering and leaving the room. Further, where multiple locations may be provided (e.g. on first and second floors, etc.), multiple weight sensing systems may be employed and the measurements combined.

The weight sensing system 410 communicates the output signals via the Internet 420 (using a wired or wireless connection for example) to a remotely located data processing system 430 (such as server).

The data processing system 430 is adapted to receive the one or more output signals from the weight sensing system 410 and process the received signal(s) in accordance with an inference/detection algorithm in order to infer/determine a trend in the weight of the person. More specifically, the algorithm processes the received sensor output signal(s) in combination with historical data relating to one or more previously detected values of the weight of the person to determine a trend in the person's weight over time. The data processing system 430 is further adapted to generate output signals representative of inferred or calculated bodyweight trend. Thus, the data processing 430 provides a centrally accessible processing resource that can receive information from the weight sensing system and run one or more algorithms to transform the received information into a description of a trend in bodyweight of the person. Information relating to the trend in bodyweight can be stored by the data processing system (for example, in a database) and provided to other components of the system. Such provision of information about a detected or inferred bodyweight trend may be undertaken in response to a receiving a request (via the internet 420 for example) and/or may be undertaken without request (i.e. 'pushed').

For the purpose of receiving information about a detected or inferred bodyweight trend from the data processing system, and thus to enable the person's bodyweight to be monitored, the system further comprises first 440 and second 450 mobile computing devices.

Here, the first mobile computing device 440 is a mobile telephone device (such as a smartphone) with a display for displaying graphical elements representative of a person's physical or mental well-being. The second mobile computing device 450 is a mobile computer such as a Laptop or Tablet computer with a display for displaying graphical elements representative of a person's bodyweight.

The data processing system 430 is adapted to communicate output signals to the first 440 and second 450 mobile computing devices via the internet 420 (using a wired or wireless connection for example). As mentioned above, this may be undertaken in response to receiving a request from the first 440 or second 450 mobile computing devices.

Based on the received output signals, the first 440 and second 450 mobile computing devices are adapted to display one or more graphical elements in a display area provided by their respective display. For this purpose, the first 440 and second 450 mobile computing devices each comprise a software application for processing, decrypting and/or interpreting received output signals in order to determine how to display graphical elements. Thus, the first 440 and second 450 mobile computing devices each comprise a processing arrangement adapted to one or more values representative of a trend, and to generate a display control signal for modifying at least one of the size, shape, position, orientation, pulsation or colour of the graphical element based on the one or more values representative of trend.

The system can therefore communicate information about an inferred or detected bodyweight trend to users of the first 440 and second 450 mobile computing devices. For example, each of the first 440 and second 450 mobile computing devices may be used to display graphical elements to a medical practitioner, a caregiver, a family member or close relative.

Implementations of the system of FIG. 4 may vary between: (i) a situation where the data processing system 430 communicates display-ready bodyweight trend data, which may for example comprise display data including graphical elements (e.g. in JPEG or other image formats) that are simply displayed to a user of a mobile computing device using conventional image or webpage display (which can be web based browser etc.); to (ii) a situation where the data processing system 430 communicates raw data set information that the receiving mobile computing device then processes to determine a trend in bodyweight, and then displays graphical elements based on the determined trend (for example, using local software running on the mobile computing device). Of course, in other implementations, the processing may be shared between the data processing system 430 and a receiving mobile computing device such that part of the data generated at data processing system 430 is sent to the mobile computing device for further processing by local dedicated software of the mobile computing device. Embodiments may therefore employ server-side processing, client-side processing, or any combination thereof.

Further, where the data processing system 430 does not 'push' information (e.g. output signals), but rather communicates information in response to receiving a request, the user of a device making such a request may be required to confirm or authenticate their identity and/or security credentials in order for the information to be communicated.

Figure 5:
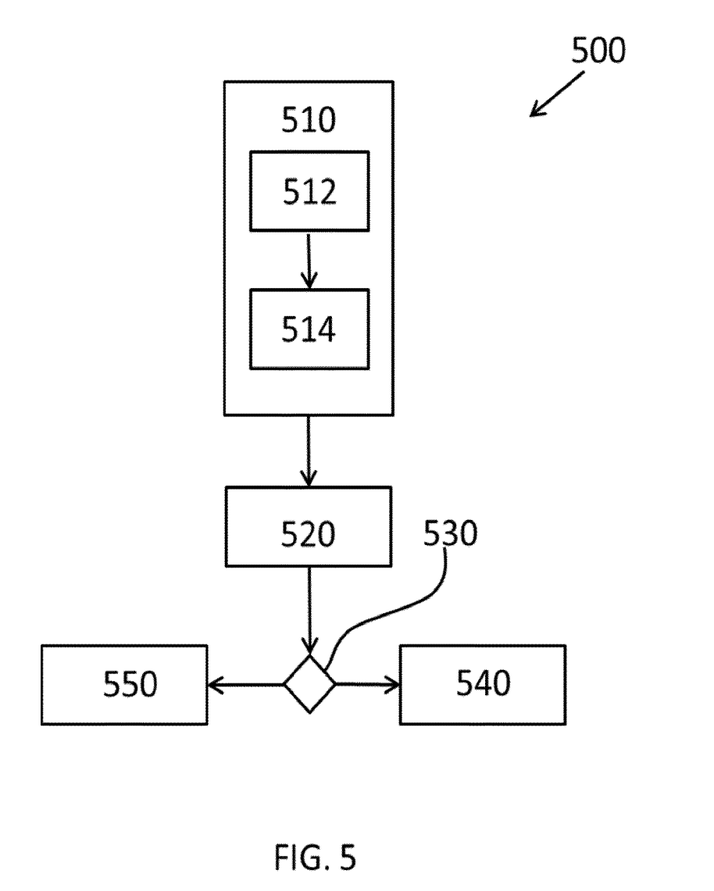
FIG. 5 shows a flow diagram of a method of monitoring a physical or mental capability of a person according to an embodiment.

Referring now to FIG. 5, there is shown a flow diagram of an exemplary method 500 of monitoring a physical or mental capability of a person.

The method begins with step 510 in which a value of a property of the person or an object manipulated by person is detected. Specifically, the step 510 of detecting a value of a property comprises the sub-steps of: determining 512 the person is positioned by a fridge door of interest; and detecting 514 a rotational velocity (or other property/quantity) of the fridge door (using a gyroscope or accelerometer arrangement for example).

Next, in step 520, a trend in the person's physical capability is determined based on the value of the detected quantity (rotational velocity of the fridge door) detected in step 514 and historical data relating to one or more previously detected values of the same quantity (e.g. rotational velocity of the fridge door) (caused by the monitored person).

Then, in step 530, the determined trend is compared with a predetermined threshold value. The threshold value can be preprogrammed, fixed or dynamically set in response to calculations based on one or more previously obtained values (e.g. using trend analysis), but is preferably also enabled to be set by a user preference. Thus, the threshold may be based on previously determined values representative of a physical or mental capability the person. In other words, the threshold may be defined by taking account of a history of the person and/or taking account of previous calculations so that it can be used to identify outlying values or anomalies. Other methods to detect outliers or to detect changes in a time series are known in the art.

If, in step 530, trend is determined to exceed the first threshold value, the method proceeds to step 540 wherein a warning signal is generated and output along with information describing the trend and/or the detected value of rotational velocity of the fridge door. If, in step 530, the trend is determined to not exceed the first threshold value, the method proceeds to step 550 wherein the information describing the trend and/or the detected value of rotational velocity of the fridge door is output without any warning signal.

Thus, by way of example, by way of example, one or more steps of the method 500 for monitoring a physical or mental capability of a person may be implemented in a portable computing device (such as the smartphone or portable computer shown in FIG. 4) in order to control the display of graphical elements on a display.

Also, in other embodiments, the trend may be extrapolated and compared against a threshold value that is associated with a future point in time. Using the extrapolated trend, one may estimate the time until the trend will cross the threshold, and provide that number as an identification of when intervention or assistance may be required, for example.

As already described above, the trend can be found as a linear line (e.g., using linear regression), but may also be curved using higher order fitting techniques.

Figure 6:
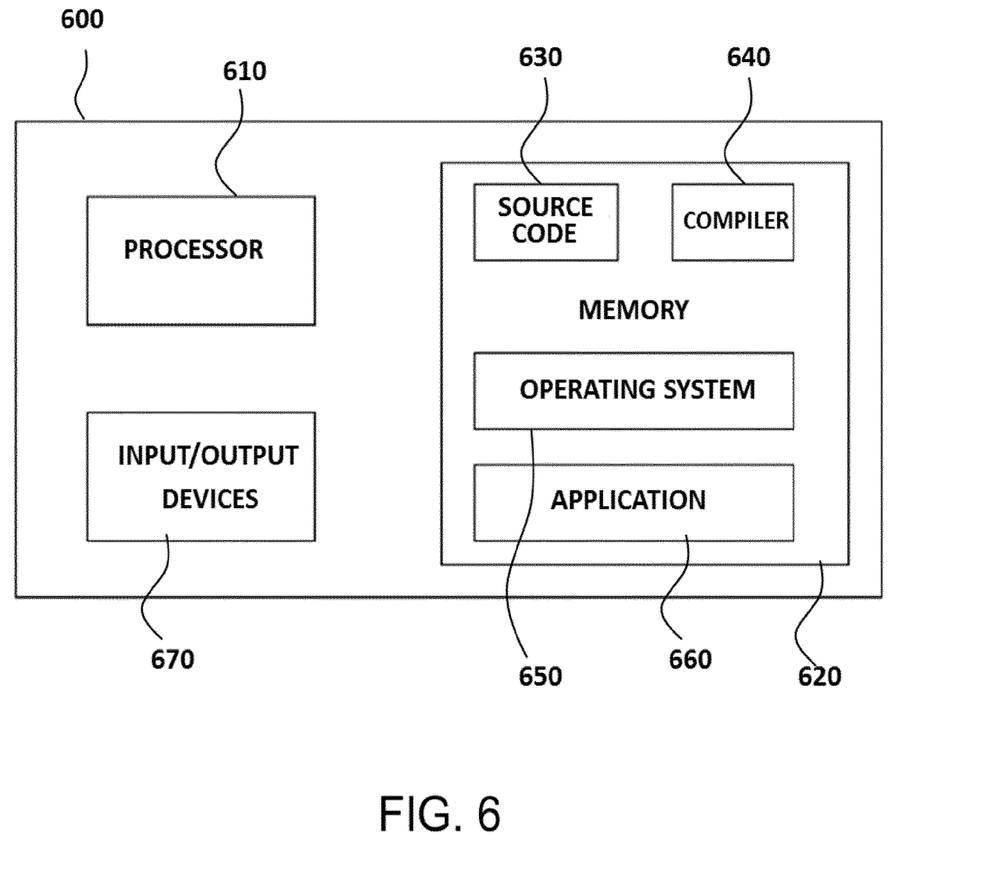
FIG. 6 is a simplified block diagram of a computer within which one or more parts of an embodiment may be employed.

FIG. 6 illustrates an example of a computer 600 within which one or more parts of an embodiment may be employed. Various operations discussed above may utilize the capabilities of the computer 600. For example, one or more parts of an ADL monitoring system adapted to monitor a physical or mental capability of a person may be incorporated in any element, module, application, and/or component discussed herein.

The computer 600 includes, but is not limited to, PCs, workstations, laptops, PDAs, palm devices, servers, storages, and the like. Generally, in terms of hardware architecture, the computer 600 may include one or more processors 610, memory 620, and one or more I/O devices 670 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 610 is a hardware device for executing software that can be stored in the memory 620. The processor 610 can be virtually any custom made or commercially available processor, a central processing unit (CPU), a digital signal processor (DSP), or an auxiliary processor among several processors associated with the computer 600, and the processor 610 may be a semiconductor based microprocessor (in the form of a microchip) or a microprocessor.

The memory 620 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 620 may incorporate electronic, magnetic, optical, and/or other types of storage media. Note that the memory 620 can have a distributed architecture, where various components are situated remote from one another, but can be accessed by the processor 610.

The software in the memory 620 may include one or more separate programs, each of which comprises an ordered listing of executable instructions for implementing logical functions. The software in the memory 620 includes a suitable operating system (O/S) 650, compiler 640, source code 630, and one or more applications 860 in accordance with exemplary embodiments. As illustrated, the application 660 comprises numerous functional components for implementing the features and operations of the exemplary embodiments. The application 660 of the computer 600 may represent various applications, computational units, logic, functional units, processes, operations, virtual entities, and/or modules in accordance with exemplary embodiments, but the application 660 is not meant to be a limitation.

The operating system 650 controls the execution of other computer programs, and provides scheduling, input-output control, file and data management, memory management, and communication control and related services. It is contemplated by the inventors that the application 660 for implementing exemplary embodiments may be applicable on all commercially available operating systems.

Application 660 may be a source program, executable program (object code), script, or any other entity comprising a set of instructions to be performed. When a source program, then the program is usually translated via a compiler (such as the compiler 640), assembler, interpreter, or the like, which may or may not be included within the memory 620, so as to operate properly in connection with the O/S 650. Furthermore, the application 660 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, Python, ADA, .NET, and the like.

The I/O devices 670 may include input devices such as, for example but not limited to, a mouse, keyboard, scanner, microphone, camera, etc. Furthermore, the I/O devices 670 may also include output devices, for example but not limited to a printer, display, etc. Finally, the I/O devices 670 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 670 also include components for communicating over various networks, such as the Internet or intranet.

If the computer 600 is a PC, workstation, intelligent device or the like, the software in the memory 620 may further include a basic input output system (BIOS) (omitted for simplicity). The BIOS is a set of essential software routines that initialize and test hardware at startup, start the O/S 650, and support the transfer of data among the hardware devices. The BIOS is stored in some type of read-only-memory, such as ROM, PROM, EPROM, EEPROM or the like, so that the BIOS can be executed when the computer 600 is activated.

When the computer 600 is in operation, the processor 610 is configured to execute software stored within the memory 620, to communicate data to and from the memory 620, and to generally control operations of the computer 600 pursuant to the software. The application 660 and the O/S 650 are read, in whole or in part, by the processor 610, perhaps buffered within the processor 610, and then executed.

When the application 660 is implemented in software it should be noted that the application 660 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 660 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A system configured to monitor an activity of daily living (ADL) and a physical or mental capability of a person, wherein the system comprises:
   a motion sensor configured to be coupled to an object manipulated by the person, detect a velocity value of a property of the object, and generate a sensor output signal representative of the detected velocity value;
   a monitor configured to receive the sensor output signal and determine a trend in the physical or mental capability of the person based on the received sensor output signal and historical data relating to one or more previously detected values of the velocity value; and
   a graphical user interface (GUI) configured to display graphical elements related to the determined trend, wherein the displayed graphical elements comprise an Area Under Curve (AUC) obtained by integrating the received sensor output signal from zero crossing to zero crossing.

2. The system according to claim 1, further comprising:
   a sensor configured to detect a measure of force applied by the person to the object;
   a sensor configured to detect a distance travelled by the object; and
   a sensor configured to detect a rate of acceleration of the object.

3. The system according to claim 1, wherein the object comprises an item of furniture.

4. The system according to claim 1, wherein the monitor is further configured to:
   detect an irregularity in the determined trend, and
   generate an alert output signal in response to the detected irregularity.

5. The system according to claim 4, wherein the monitor is further configured to detect the irregularity based on a comparison of the determined trend with a threshold value.

6. The system according to claim 5, wherein the threshold value is determined based on at least one of:
   one or more previously detected values of the property; and
   one or more previously determined changes in values of the property.

7. The system according to claim 1, further comprising:
   an accelerometer;
   a gyroscope;
   a weight sensor;
   a pressure sensor; and
   a timing device.

8. The system according to claim 1, wherein the monitor is further configured to:
   calculate an estimated future value of the property based on the determined trend,
   detect an irregularity based on a comparison of the estimated future value of the property with a threshold value, and
   generate an alert output signal in response to the detected irregularity.

9. The system according to claim 1, wherein the monitor is further configured to generate a control signal for modifying the graphical elements based on the determined trend in the physical or mental capability of the person.

10. The system of claim 1, wherein the monitor is remotely located from the sensor, and a signal representative of the detected value of the property is communicated to the monitor via a communication link.

11. A method of monitoring a physical or mental capability of a person, wherein the method comprises:
    detecting a velocity value of a property of an object manipulated by the person;
    determining a trend in the physical or mental capability of the person based on the detected velocity value of the property and historical data relating to one or more previously detected velocity values of the property; and
    displaying, with a graphical user interface (GUI), graphical elements related to the determined trend, wherein the displayed graphical elements comprise an Area Under Curve (AUC) obtained by integrating the received sensor output signal from zero crossing to zero crossing.

12. The method of claim 11, further comprising:
    detecting a measure of force applied by the person to the object;
    detecting a distance travelled by the object; and
    detecting a rate of acceleration of the object.

13. The method of claim 11, further comprising:
    detecting an irregularity in the determined trend, and
    generating an alert output signal in response to the detected irregularity.

14. The method of claim 13, wherein the step of detecting the irregularity further comprises:
    calculating an estimated future value of the property based on the determined trend;
    detecting the irregularity based on a comparison of the estimated future value of the property with a threshold value.

15. A non-transitory computer readable medium comprising computer readable code that when executed on a computer causes the computer to:
    detect a velocity value of a property of an object manipulated by the person; and
    determine a trend in the physical or mental capability of the person based on the detected velocity value of the property and historical data relating to one or more previously detected velocity; and values
    display, with a graphical user interface (GUI), graphical elements related to the determined trend, wherein the displayed graphical elements comprise an Area Under Curve (AUC) obtained by integrating the received sensor output signal from zero crossing to zero crossing.

* * * * *